United States Patent [19]

Etherton et al.

[11] Patent Number: 5,539,124
[45] Date of Patent: Jul. 23, 1996

[54] POLYMERIZATION CATALYSTS BASED ON TRANSITION METAL COMPLEXES WITH LIGANDS CONTAINING PYRROLYL RING

[75] Inventors: Bradley P. Etherton, Houston, Tex.; Sandor Nagy, Grand Island, N.Y.

[73] Assignee: Occidental Chemical Corporation, Niagara Falls, N.Y.

[21] Appl. No.: 358,492

[22] Filed: Dec. 19, 1994

[51] Int. Cl.$^6$ .................... C07D 207/00; C07D 209/00; C07F 7/00; B01J 31/00

[52] U.S. Cl. .................. 548/402; 502/103; 502/117; 502/118; 502/152; 556/56; 556/54; 556/53; 556/52

[58] Field of Search ..................... 502/103, 117, 502/118, 152; 556/51, 52, 53, 54, 56; 548/402

[56] References Cited

U.S. PATENT DOCUMENTS

| | | | |
|---|---|---|---|
| 5,376,612 | 12/1994 | Reagen et al. | 502/117 |
| 5,382,738 | 1/1995 | Reagen et al. | 502/117 |
| 5,434,116 | 7/1995 | Sone et al. | 502/117 |

FOREIGN PATENT DOCUMENTS 0574794  12/1993  European Pat. Off. .

OTHER PUBLICATIONS

King, *Inorganic Chemistry* (1964), 3, 796.
Joshi, *Journal of Organometallic Chemistry* (1964), 1, 471.
VanBynum et al., *Canadian Journal of Chemistry* (1986), 64, 1304.
Ladipo et al., *Inorganic Chemistry* (1990), 29, 4172.
J. Zakrzewski, *Heterocycles* (1990), 31, 383.

Primary Examiner—Anthony McFarlane
Assistant Examiner—J. Pasterczyk
Attorney, Agent, or Firm—Wayne A. Jones; Richard D. Fuerle

[57] ABSTRACT

Disclosed is an azametallocene polymerization catalyst having the general formula

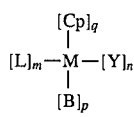

where L is a ligand, or mixture of ligands, each having 4 to 30 carbon atoms and containing at least two fused rings, one of which is a pyrrolyl ring, Cp is a ligand containing a cyclopentadienyl group, B is a Lewis acid, Y is a halogen, alkoxy from $C_1$ to $C_{20}$, siloxy from $C_1$ to $C_{20}$, or mixtures thereof, M is titanium, zirconium, or mixtures thereof, m is 1 to 4, and n is 0 to 2, p is 0 to 2, q is 0 to 1, and m+n+q=4. The catalyst is useful in polymerizing unsaturated olefinic monomers such as ethylene.

22 Claims, No Drawings

POLYMERIZATION CATALYSTS BASED ON TRANSITION METAL COMPLEXES WITH LIGANDS CONTAINING PYRROLYL RING

BACKGROUND OF THE INVENTION

This invention relates to azametallocene catalysts useful for polymerizing olefins such as ethylene and other unsaturated monomers. In particular, it relates to catalysts having at least one ligand that contains a pyrrolyl ring bonded to a transition metal.

Until recently, polyolefins have been primarily made with conventional Ziegler catalyst systems. These catalysts typically consist of transition metal-containing compounds and one or more organometallic compound. For example, polyethylene has been made using Ziegler catalysts such as titanium trichloride and diethylaluminum chloride, or a mixture of titanium tetrachloride, vanadium oxytrichloride, and triethylaluminum. These catalysts are inexpensive but they have low activity and therefore must be used at high concentrations. As a result, it is sometimes necessary to remove catalyst residues from the polymer, which adds to production costs. Neutralizing agents and stabilizers must be added to the polymer to overcome the deleterious effects of the catalyst residues. Failure to remove catalyst residues leads to polymers having a yellow or grey color and poor ultraviolet and long term stability. For example, chloride-containing residues can cause corrosion in polymer processing equipment.

Furthermore, Ziegler catalysts produce polymers having a broad molecular weight distribution, which is undesirable for some applications such as injection molding. They are also poor at incorporating α-olefin comonomers. Poor comonomer incorporation makes it difficult to control the polymer density. Large quantities of excess comonomer may be required to achieve a certain density and many higher α-olefins, such as 1-octene, may be incorporated at only very low levels, if at all.

Although substantial improvements in Ziegler catalyst systems have occurred since their discovery, these catalysts are now being replaced with the recently discovered metallocene catalyst systems. A metallocene catalyst typically consists of a transition metal compound which has one or more cyclopentadienyl ring ligands. They have low activities when used with organometallic compounds, such as aluminum alkyls, which are used with traditional Ziegler catalysts, but very high activities when used with aluminoxanes as cocatalysts. The activities are generally so high that catalyst residues need not be removed from the polymer. Furthermore, they produce polymers with high molecular weights and narrow molecular weight distributions. They also incorporate α-olefin comonomers well. However, at higher temperatures metallocene catalysts tend to produce lower molecular weight polymers. Thus, they are useful for gas phase and slurry polymerizations of ethylene, which are conducted at about 80° C. to about 95° C., but they do not generally work well in solution polymerizations of ethylene, at about 150° C. to about 250° C. The polymerization of ethylene in solution is desirable because it allows great flexibility for producing polymers over a wide range of molecular weights and densities as well as the use of a large variety of different comonomers. One can produce polymers that are useful in many different applications, for example, high molecular weight, high density polyethylene film useful as a barrier film for food packaging and low density ethylene copolymers with good toughness and high impact strength.

One of the characteristics of metallocene catalysts is the presence of π-bonds between one or more cyclopentadienyl ring-containing ligands and a transition metal. These bonds are moderately strong and stable. In contrast, π-bonds between transition metals and pyrrolyl ring-containing ligands are relatively unstable. Although these nitrogen-containing ligands form unstable π-bonds, analogous ligands with other Group VA elements (P, As) form stable bonds. King (*Inorg. Chem.*, 1964, 3, 796) and Joshi (*J. Organomet. Chem.*, 1964, 1, 471) found that the pyrrolyl analog of ferrocene was less stable and had indications that pyrrolyl ligands tended to form σ-bonds. Van Bynum et al. prepared 2,5-dimethylpyrrole derivatives of Zr and showed that there was no π-bonding to the Zr atoms in these compounds (*Can. J. Chem.*, 1986, 64, 1304). Ladipo et al. showed that indole complexes with iridium also formed σ-bonds to the transition metal (*Inorg. Chem.*, 1990, 29, 4172). A recent review of the subject of π-bonded pyrrolyl-containing ligands (J. Zakrezewski, *Heterocycles*, 1990, 31, 383) reemphasized the instability of these types of complexes.

SUMMARY OF THE INVENTION

We have discovered certain novel azametallocene compounds which are useful as polymerization catalysts over a wide range of polymerization conditions. These compounds all have at least one ligand containing a pyrrolyl group, which is a nitrogen-containing 5-membered resonance ring. The pyrrolyl group can form a bond to a transition metal atom. These compounds are used in conjunction with a cocatalyst which is typically an alumoxane. It is surprising that compounds containing a pyrrolyl group are useful as polymerization catalysts because it is well known in the catalyst art that nitrogen-containing compounds are frequently catalyst poisons. However, we have found that not only are these compounds useful as olefin polymerization catalysts, but that they have good activity at high temperatures and produce high molecular weight polymers with narrow molecular weight distributions.

The catalysts of this invention perform as well as conventional metallocenes in incorporating comonomers such as butene, octene, hexene, and 4-methylpentene-1. They produce colorless polymers having superior UV stability and long term stability. In addition, the catalysts of this invention are considerably simpler to prepare and are less expensive than the analogous metallocenes.

DESCRIPTION OF THE PREFERRED EMBODIMENTS

The catalysts of this invention are transition metal compounds having the general formula

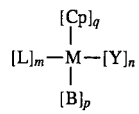

where L is a ligand, or mixture of ligands, each having 4 to 30 carbon atoms and containing at least two fused rings, one of which is a pyrrolyl ring, Cp is a ligand containing a cyclopentadienyl ring, where two L ligands or an L and a Cp ligand can be bridged, B is a Lewis base, Y is halogen, alkoxy from $C_1$ to $C_{20}$, siloxy from $C_1$ to $C_{20}$, $N(R_1)_2$, or mixtures thereof, M is titanium, zirconium, or mixtures thereof, m is a number from 1 to 4, n is a number from 0 to 2, p is a number from 0 to 2, q is a number from 0 to 1, and m+n+q=4. In the formula, Y is preferably halogen and is more preferably either chlorine or bromine, but alkoxy groups, such as methoxy ($CH_3O-$), ethoxy ($CH_3CH_2O-$), or siloxy ($(R_1)_3SiO-$), where $R_1$ is alkyl from $C_1$ to $C_{20}$, should also be mentioned. Also, m is preferably 4 as those catalysts produce polymers having the highest molecular weight at the highest temperature.

Examples of L groups that can be used include alkyl substituted pyrrolyl rings,

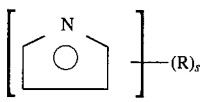

such as 2-methylpyrrolyl, 3-methylpyrrolyl, 2,5-dimethylpyrrolyl, 2,5-di-tert-butylpyrrolyl, aryl substituted pyrrolyl rings such as 2-phenylpyrrolyl, 2,5-diphenylpyrrolyl, indolyl, alkyl substituted indolyls

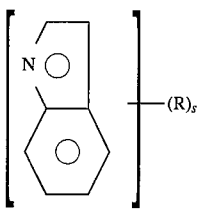

such as 2-methylindolyl, 2-tert-butylindolyl, 3-butylindolyl, 7-methylindolyl, 4,7-dimethylindolyl, aryl substituted indolyls such as 2-phenylindolyl, 3-phenylindolyl, 2-naphthylindolyl, isoindolyl, and alkyl and aryl substituted isoindolyls

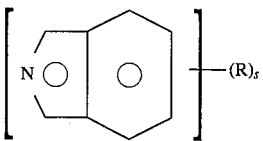

and carbazolyl and alkyl substituted carbazolyls

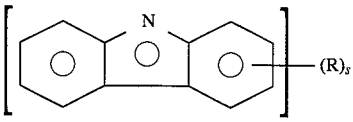

In the formulas, each R is preferably independently selected from hydrogen, alkyl from $C_1$ to $C_{10}$, and aryl from $C_6$ to $C_{10}$ and S is 1 to 4. The alkyl and aryl substituents on the pyrrolyl ring-containing ligand are not on the nitrogen atom in the ring but are on the carbon atoms of the ring. Particularly preferred L ligands are the carbazolyl and $C_1$ to $C_4$ alkyl indolyls in the 2 or 7 position, or in both positions, because an alkyl in the 2 position prevents the formation of dimers. Carbazolyl- and indolyl-based catalysts produce high activity and superior performance at high polymerization temperatures, giving high molecular weights which means a tougher polymer and better impact strength and better tensile properties. The formulas exclude the use of only non-bridged unsubstituted pyrrolyl groups and non-bridged substituted pyrrolyl groups as the ligand because those catalysts do not seem to work well (see Comparative Examples).

Examples of Lewis bases, B, which can be used in this invention include diethyl ether, dibutyl ether, tetrahydrofuran, and 1,2-dimethoxyethane. The Lewis base B is residual solvent and the bond between B and M is not a covalent bond.

The Cp ligand can be a cyclopentadienyl ring with 0 to 5 substituent groups,

where each substituent group, $R_2$, is independently selected from a $C_1$ to $C_{20}$ hydrocarbyl group and r is a number from 0 to 5. In the case in which two $R_2$ groups are adjacent, they can be joined to produce a ring which is fused to the Cp ring. Examples of alkyl substituted Cp rings include butyl cyclopentadienyl, methyl cyclopentadienyl, and pentamethylcyclopentadienyl. Examples of fused Cp ring ligands include indenyl, tetrahydroindenyl, fluorenyl, and 2-methylindenyl. While the Cp ligand can be used in combination with other ligands, it is preferably not present as it seems to lower the molecular weight of polyethylene made at higher temperatures.

Groups that can be used to bridge two ligands include methylene, ethylene, 1,2-phenylene, dimethyl silyl, diphenyl silyl, diethyl silyl, and methyl phenyl silyl. Normally, only a single bridge is used in a catalyst. It is believed that bridging the ligand changes the geometry around the catalytically active transition metal and improves catalyst activity and other properties, such as comonomer incorporation and thermal stability.

The catalysts of this invention can be prepared in a variety of ways, but they are most easily prepared by starting with a ligand compound. Most of the compounds used as ligands are commercially available, including indole, pyrrole, and carbazole, as well as some alkyl indoles. Substituted ligands can be made by a variety of methods. Some examples include Friedel-Crafts alkylation, alkylation with lithium alkyls, direct synthesis via the Fischer indole synthesis, and the methods described by Bray et al. in *J. Org. Chem.*, 1990, 55, 6317. A number of other methods are known to those skilled in the art.

In the first step in producing the catalyst, the ligand compound is reacted with a proton acceptor. Stoichiometric quantities can be used. Examples of proton acceptors include methylmagnesium bromide, sodium hydride, sodium metal, and methylmagnesium chloride. The preferred proton acceptor is methyl magnesium bromide because of ease of use. The reaction is preferably performed by dissolving the reactants in an organic solvent that does not have active proton, such as tetrahydrofuran, anisole, or ethyl ether. An ether, such as diethylether, is preferred. The solution should be as concentrated as possible to reduce the amount of solvent that must be handled. The reaction can occur at about $-78°$ to about $50°$ C. but is preferably performed at about $-10°$ to $25°$ C. in order to avoid heating. The reaction is over when gas evolution ceases. For example, indole reacts with methyl magnesium bromide to produce methane gas and a solution of an indolyl ligand in the solvent:

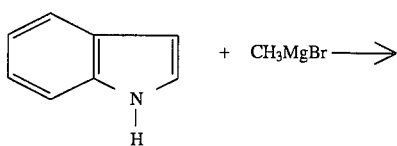

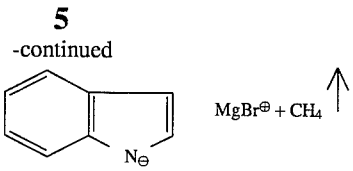

In the next step of the process for making the catalysts of this invention, a transition metal halide, alkoxide, or siloxide is added to the solution of the ligand compound at a temperature between about −100° and about 0° C. Higher temperatures should be avoided as they may cause decomposition of the metal ligand product. Stoichiometric quantities of the reactants can be used. The reaction between the ligand compound and the transition metal compound results in the production of the metal ligand catalyst and precipitation of a proton acceptor byproduct, such as magnesium halide. For example, if zirconium tetrachloride is reacted with the indolyl ligand prepared as described in the previous paragraph, the metal ligand catalyst is produced and magnesium halides precipitate:

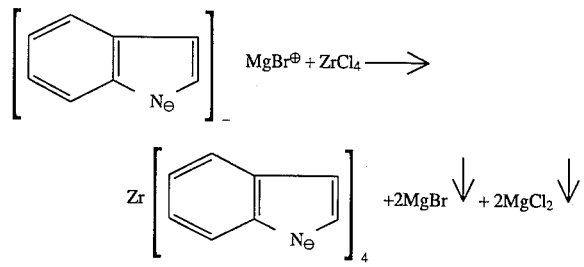

The byproducts are removed by filtration, the solvent is evaporated, and the metal ligand catalyst is collected. While we do not wish to be bound by any theory, we believe that the catalysts of this invention are single site catalysts because they produce polymers with a ratio of weight average molecular weight to number average molecular weight very close to 2. The polymers have a narrow molecular weight distribution.

Alternatively, the azametallocene polymerization catalysts of this invention can be prepared in a three step procedure, by first stoichiometrically reacting in a solvent a Group I or II metal dialkylamide with a titanium or zirconium compound:

$(4-q)M'N(R_1)_2 + M(R_3)_{4-q}(Cp)_q \rightarrow M(N(R_1)_2)_{4-q}(Cp)_q + (4-q)M'R_3 \downarrow$ where M' is an alkali or alkaline earth metal, preferably lithium, sodium, or magnesium as those metal dialkylamides are readily available, and $R_3$ is halide, preferably chloride, or alkoxide from $C_1$ to $C_8$. The $R_1$ (alkyl from $C_1$ to $C_{20}$) group is preferably $C_2$ to $C_6$ as those compounds are more available. The reaction temperature is not critical and a temperature between −10° and 50° C., such as room temperature, is suitable. The reaction is complete when the alkali metal or alkaline earth metal byproduct, such as lithium chloride, precipitates. Since many tetrakis(dialkylamido)titanium and zirconium compounds are commercially available, this first reaction is not always necessary.

In the second step of the alternative preparation procedure, the tetrakis(dialkylamido)titanium or zirconium compound is reacted with a compound that contains a pyrrole ring:

$M(N(R_1)_2)_{4-q}(Cp)_q + mLH \rightarrow (L)_sM(N(R_1)_2)_{4-m-q}(Cp)_q + mNH(R_1)_2$

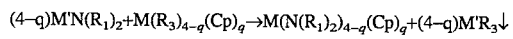

This reaction will occur over a wide range of temperatures in various solvents including xylene, diethyl ether, tetrahydrofuran, and dimethoxyethane, but hydrocarbon solvents, such as toluene, are preferred. Preferably, the reaction temperature is about −78° C. to about 50° C. Completion of the reaction is indicated by gas evolution or the detection of free base using nuclear magnetic resonance (NMR).

In the third step of the alternative preparation procedure, the product of the second step is reacted with a compound that replaces some or all of the remaining amido groups with halogen, alkoxy, or siloxy groups:

$(L)_mM(N(R_1)_2)_{4-m-q}(Cp)_q + nYZ \longrightarrow$

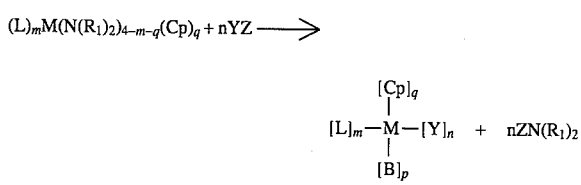

where Z is the cationic portion of the YZ compound. Treatment with a halogenating agent replaces the amido groups with halogen. Halogenating agents include such compounds as silicon tetrachloride, hydrogen chloride, methyltrichlorosilane, boron trichloride, hexachloroethane, phosphorus pentachloride, antimony pentachloride, chlorine, and the like. For example, treatment of bis(carbazolyl)-bis(diethylamido)zirconium with two moles of silicon tetrachloride produced bis(carbazolyl)zirconium dichloride.

Since the catalyst is normally used in conjunction with a co-catalyst, it is preferable to dissolve the metal compound in a solvent in which the co-catalyst is also soluble. For example, if methylalumoxane (MAO) is the co-catalyst, then toluene, xylene, benzene, or ethyl benzene could be used as the solvent. Examples of suitable co-catalysts include MAO and mixtures of MAO with other aluminum alkyls such as triethylaluminum, trimethylaluminum, tri-isobutylaluminum, ethylalumoxane, or diisobutyl alumoxane. The preferred co-catalyst is MAO as it results in high catalyst activity, good comonomer incorporation, and a polymer having a narrower molecular weight distribution. It is preferable not to premix the catalyst and the co-catalyst as this may result in lower catalyst activity. Rather, the catalyst and co-catalyst are preferably injected separately into a reactor containing the monomer to be polymerized. And, preferably, the co-catalyst is injected first. The amount of cocatalyst used with the transition metal compound can be in a molar ratio ranging from about 1:1 to about 15,000:1.

The catalyst and co-catalyst can also be used on a support such as silica gel, alumina, magnesia, or titania. Supports are not generally preferred as they leave additional contaminants in the polymer. However, a support may be required depending upon the process being utilized. For example, a support is generally needed in gas phase polymerization processes and slurry polymerization processes in order to control the particle size of the polymer being produced and in order to prevent fouling of the reactor walls. In order to use a support, the catalyst is dissolved in a solvent and is deposited onto the support material by evaporating the solvent. The cocatalyst can also be deposited on the support or it can be introduced into the reactor separately from the supported catalyst.

Once the catalyst has been prepared it should be used as promptly as possible as it may lose some activity during storage. Storage of the catalyst should be at a low temperature, such as −100° C. to 20° C. The catalyst is used in a conventional manner in the polymerization of unsaturated olefinic monomers. While unsaturated monomers such as styrene can be polymerized using the catalysts of this invention, it is particularly useful for polymerizing α-olefins such as propylene, 1-butene, 1-hexene, 1-octene, and especially ethylene.

The catalyst is also useful for copolymerizing mixtures of ethylene with unsaturated monomers such as 1-butene, 1-hexene, 1-octene, and the like; mixtures of ethylene and di-olefins such as 1,3-butadiene, 1,4-hexadiene, 1,5-hexadiene, and the like; and mixtures of ethylene and unsaturated comonomers such as norbornadiene, ethylidene norbornene, vinyl norbornene, and the like.

The catalysts of this invention can be utilized in a variety of different polymerization processes. They can be utilized in a liquid phase polymerization process (slurry, solution, suspension, bulk phase, or a combination of these), in a high pressure fluid phase, or in a gas phase polymerization process. The processes can be used in series or as individual single processes. The pressure in the polymerization reaction zones can range from about 15 psia to about 50,000 psia and the temperature can range from about −100° C. to about 300° C.

The following examples further illustrate this invention.

EXAMPLE 1

Catalyst Preparation

All steps were conducted under a nitrogen atmosphere using conventional Schlenk-line techniques. All glassware was clean and free of moisture and oxygen. All solvents were freed of water, air, and other impurities. This was done by passage over activated basic alumina, collection under nitrogen, sparging with nitrogen, and storage over activated 4A molecular sieves.

Indole (from Aldrich Chemical Company) was recrystallized from hexane. Recrystallized indole (2.34 g) was placed in a 250 ml Schlenk flask which contained a stirring bar and the flask was sealed with a septum. Diethyl ether (50 ml) was added by double-ended needle to dissolve the indole. The indole solution was cooled to 0° C. in an ice bath. Methylmagnesium bromide (6.70 ml, 3.0 molar) in ether (from Aldrich Chemical Company) was added slowly by syringe while stirring. Gas evolved during this addition. The reaction mixture was stirred for 1 hour. The ice bath was removed and the mixture was allowed to warm to room temperature while stirring. The mixture was stirred an additional 1 hour at room temperature.

Zirconium tetrachloride (2.33 g) from Aldrich Chemical Company and used without further purification, was placed in a clean, dry, oxygen-free 250 ml Schlenk flask which contained a stirring bar. The flask was sealed with a septum. Diethyl ether (100 ml) was added by double ended needle. This suspension was cooled to 0° C. in an ice bath. The indole/methylmagnesium bromide product was added to the ZrCl$_4$ suspension over 10 minutes using a double ended needle. The reaction mixture was stirred for 1 hour. The ice bath was removed and the mixture was allowed to warm to room temperature while stirring. The mixture was stirred an additional hour at room temperature. The product was an orange slurry. The ether was removed from the slurry by evaporation under vacuum. The product was a brown solid. Toluene (100 ml) was added to this solid and stirred for 2 hours at room temperature. The solution was recovered by vacuum filtration using a fine (4 micron) fritted glass filter. The toluene was removed by evaporation under vacuum. The product was a solid which contained 6.0 wt % Zr. Elemental analysis did not show the presence of Cl.

Polymerization Results

Polymerizations were conducted in a stirred 1.7 liter stainless steel autoclave at 80° C. Dry oxygen-free toluene (840 ml) was charged to the clean, dry oxygen-free reactor. Six ml of 10% MAO in toluene (from Ethyl Corporation and used without further purification) was added to the toluene in the reactor. No hydrogen or comonomer was added to the reactor. Sufficient ethylene was added to bring the reactor pressure to 150 psig. A solution of catalyst was prepared by dissolving 0.3604 grams of product in 100 ml of toluene. Three ml of this solution was injected into the reactor to start a polymerization.

At the end of one hour the ethylene flow was stopped and the reactor was rapidly cooled to room temperature. The polymer was filtered from the toluene by vacuum filtration. It was dried overnight in a vacuum oven and weighed. The weight of the polymer was 75.2 grams. This corresponded to a catalyst productivity of 69.9 kg/g Zr.

Polymer Properties

The melt index of the polymer was measured according to ASTM D-1238, Condition E and Condition F. MI is the melt index measured with a 2.16 kg weight (Condition E). HLMI is the melt index measured with a 21.6 kg weight (Condition F). MFR is the ratio of HLMI to MI. The polymer density was measured according to ASTM D-1505. The molecular weight distribution of the polymer was measured using a Waters 150C gel permeation chromatograph at 135° C. with 1,2,4-trichlorobenzene as the solvent. Both weight average molecular weight ($M_w$) and ratio of $M_w$ to $M_n$ (number average molecular weight) are used to characterize the molecular weight distribution.

The polymer melting point was measured using a DuPont Instruments 912 differential scanning calorimeter (DSC). Two heating and cooling cycles were utilized. The melting point was measured on the second heating/cooling cycle. The heating and cooling rates were 10° C./min. Between the two cycles, the sample was held at 200° C. for 10 minutes before cooling to 50° C.

The polymer had a MI of 0.086 dg/min and HLMI of 1.82 dg/min. This corresponds to a MFR of 21.2. $M_w$ was 162,400 and $M_w/M_n$ was 2.06. This indicates a narrow molecular weight distribution even though the molecular weight was high. The density was 0.9536 g/ml. The DSC melting point was 136.0° C.

EXAMPLE 2

This example shows that the catalyst can be used with low levels of MAO to produce a high molecular weight polymer. The very high levels of MAO typically used with metallocene catalysts are not needed. The catalyst described in Example 1 was tested under the same polymerization conditions as Example 1 except that 3.0 ml of 10% MAO was used. A one hour polymerization resulted in 26.1 grams of polyethylene. The polymer had a MI of 0.068 dg/min and HLMI of 1.53 dg/min. This corresponds to a MFR of 22.5.

EXAMPLE 3

This example shows that the catalyst can be used at high temperatures to produce high molecular weight polymers. The catalyst described in Example 1 was tested under the same polymerization conditions as in Example 2 except that the temperature was 110° C. The amount of polyethylene produced was 38.9 grams. The polymer had a MI of 0.90 dg/min and HLMI of 15.93 dg/min. This corresponds to a MFR of 17.7. $M_w$ was 102,800 and $M_w/M_n$ was 1.91. The polymer density was 0.9606 g/ml. The DSC melting point was 135.8° C.

EXAMPLE 4

This example shows the effect of higher temperatures and higher levels of MAO on the performance of the catalyst described in Example 1. The catalyst was tested under the same polymerization conditions as in Example 1 except that the temperature was 110° C. The amount of polyethylene produced was 71.3 grams. The polymer had a MI of 1.77 dg/min and HLMI of 32.2 dg/min. This corresponds to a MFR of 18.2. $M_w$ was 79,600 and $M_w/M_n$ was 1.68. The polymer density was 0.9601 g/ml. The DSC melting point was 134.9° C.

EXAMPLE 5

This examples shows the effect of using a different MAO as cocatalyst with the catalyst described in Example 1. The catalyst was tested under the same polymerization conditions as in Example 3 except that 6.0 ml of polymethylalumoxane (PMAO) S2 (from Akzo Chemical and used without further purification) was used as the cocatalyst. This sample contained 4.3 mole/liter of aluminum. The amount of polyethylene produced was 81.9 grams. The polymer had a MI of 3.69 dg/min.

EXAMPLE 6

The catalyst described in Example 1 was tested under the polymerization conditions described in Example 4 except that 20.0 ml of liquid 1-butene was added to the reactor. The amount of polyethylene produced was 88.9 grams. The polymer had a MI of 11.79 dg/min and HLMI of 233.4 dg/min. This corresponds to a MFR of 19.8.

EXAMPLE 7

Catalyst Preparation

The catalyst was prepared using the methods described in Example 1. Recrystallized indole (2.34 grams) was placed in a 250 ml Schlenk flask which contained a stirring bar. The flask was sealed with a septum. Diethyl ether (100 ml) was added by double-ended needle to dissolve the indole. The solution was cooled to 0° C. in an ice bath. Methylmagnesium bromide in ether (6.70 ml, 3.0 molar) was dissolved in 50 ml of ether. The methylmagnesium bromide solution was added slowly to the indole solution by double-ended needle while stirring. Gas evolved during this addition. The reaction mixture was stirred for 1 hour. The ice bath was removed and the mixture was allowed to warm to room temperature while stirring. The mixture was stirred an additional 1 hour at room temperature.

Titanium tetrachloride (1.10 ml) from Aldrich Chemical and used without further purification, was placed in a clean, dry, oxygen-free 250 ml Schlenk flask which contained a stirring bar. The flask was sealed with a septum and 100 ml of ether was added by double-ended needle. This was stirred overnight at room temperature to produce a yellow solution. This solution was cooled to 0° C. in an ice bath. The indole/methylmagnesium bromide product was added to the $TiCl_4$ solution over 10 minutes using a double-ended needle. The reaction mixture was stirred for 30 minutes, then the ice bath was removed and the mixture was allowed to warm to room temperature. The mixture was stirred two hours at room temperature. The product was a black slurry. The ether was removed from the slurry by evaporation under vacuum to recover a black solid.

Polymerization Testing

A solution of the product was prepared by dissolving 0.500 grams of solid in 100 ml dry, oxygen-free toluene. After stirring for 1 hour the sample was not completely dissolved. An analysis of the liquid phase showed a Ti concentration of $5.01 \times 10^{-3}$ moles/liter. Polymerizations were conducted as described in Example 1, except that 3.4 ml of 10% MAO in toluene was added as a cocatalyst and 30 millimoles of hydrogen were added. No comonomer was added to the reactor. One ml of the catalyst solution was used to start a polymerization and 35.1 grams of polymer was produced after one hour. The polymer had a MI of 0.125 dg/min and a HLMI of 4.75 dg/min. This corresponds to a MFR of 38.0.

EXAMPLE 8

This example shows the effect of different MAO amounts on the catalyst activity. Solid (0.450 grams) from Example 7 was dissolved in 100 ml of toluene. The polymerization conditions were identical to those of Example 7 except that 3.0 ml of catalyst solution and 10.0 ml of MAO solution were used. In addition, 120 millimoles of hydrogen were added. After one hour 50.1 grams of polymer was produced.

EXAMPLE 9

This example shows the effect of increased hydrogen and 1-butene on the catalyst activity. The polymerization described in Example 8 was repeated except that 12 ml of liquid 1-butene and 120 millimoles of hydrogen were added to the reactor. In 30 minutes 55.5 grams of polymer was produced.

EXAMPLE 10

This example shows the effect of increased hydrogen alone on the catalyst activity. The polymerization described in Example 8 was repeated except that 180 millimoles of hydrogen was added to control the molecular weight. In 30 minutes 54.9 grams of polymer was produced.

EXAMPLE 11

Catalyst Preparation

The catalyst was prepared using the methods described in Example 1. 2-Methylindole, (2.59 grams) from Aldrich Chemical Company and used without further purification, was placed in a 250 ml Schlenk flask which contained a stirring bar. The flask was sealed with a septum. Diethyl ether (70 ml) was added by double-ended needle to dissolve the 2-methylindole. Methylmagnesium bromide (6.70 ml, 3.0 molar) in ether was placed in a 4 oz. bottle and 40 ml of diethyl ether was added to dissolve it.

The 2-methylindole solution was cooled in an ice bath at 0° C. The methylmagnesium bromide solution was added to the indole with a double-ended needle over 15 minutes. Gas evolved during this addition. The reaction mixture was stirred for 30 minutes at 0° C. The ice bath was removed and the mixture warmed to room temperature over 90 minutes. This product was stored overnight at 10° C.

Titanium tetrachloride (1.10 ml) was placed in a dry, oxygen-free 4 oz. bottle which contained a stirring bar. Toluene (40 ml) was added to the bottle which was then sealed with a septum. The Schlenk flask containing the reaction product of 2-methylindole and methylmagnesium bromide was cooled to 0° C. in an ice bath for 15 minutes. The TiCl$_4$ solution was added via double-ended needle over about 15 minutes while stirring. The reaction mixture was stirred for about 2.5 hours at 0° C. The ice bath was then removed and the mixture allowed to warm to room temperature while stirring. The flask was stored at 10° C. overnight. The product was a reddish-black slurry.

The ether was removed from the slurry by evaporation under vacuum. The product was a black solid. Approximately 100 ml of toluene was added to this solid and stirred for one hour at room temperature. This resulted in a reddish black slurry. The solids were filtered off using a fine fritted filter and the solution was collected. The toluene was removed by evaporation under vacuum giving a black solid which contained 7.9 wt % Ti.

Polymerization Testing

A solution of the product was prepared by dissolving 0.4501 grams in 100 ml of toluene. Polymerizations were conducted as described in Example 1, except that 10.0 ml of 10% MAO in toluene was added as a cocatalyst and the polymerization was conducted at 80° C. with 3.0 moles of hydrogen added. Three ml of the catalyst solution was used to start a polymerization and 12.5 grams of polymer was produced after one hour. The polymer had a MI of 0.048 dg/min and a HLMI of 3.04 dg/min. This corresponds to a MFR of 63.2.

EXAMPLE 12

The polymerization described in Example 11 was repeated except that the amount of catalyst used was 1.5 ml of catalyst solution and 180 millimoles of hydrogen were added to the reactor. In one hour 14.4 grams of polymer was produced. The polymer had a MI of 0.393 dg/min and a HLMI of 7.78 dg/min. This corresponds to a MFR of 19.8.

EXAMPLE 13

Catalyst Preparation

The catalyst was prepared using the methods described in Example 1. 2-Methylindole (2.69 grams) from Aldrich Chemical Company and used without further purification, was placed in a 250 ml Schlenk flask which contained a stirring bar. The flask was sealed with a septum. Diethyl ether (40 ml) was added by double-ended needle to dissolve the 2-methylindole. Methylmagnesium bromide (6.70 ml, 3.0 molar) in ether was placed in a 4 oz. bottle and 30 ml of diethyl ether was added to dissolve it.

The 2-methylindole solution was cooled in an ice bath at 0° C. The methylmagnesium bromide solution was added to the indole with a double-ended needle over 10 minutes. Gas evolved during this addition. The reaction mixture was stirred for 2 hours at 0° C. The ice bath was removed and the mixture was stored overnight at 10° C.

Zirconium tetrachloride (2.30 grams) was placed in a dry, oxygen-free 250 ml Schlenk flask which contained a stirring bar. Diethyl ether (120 ml) was added and the flask was sealed with a septum. The flask was stirred for two hours at room temperature and then cooled to 0° C. in an ice bath.

The reaction product of 2-methylindole and methylmagnesium bromide was added to the ZrCl$_4$ slurry via double-ended needle over about 20 minutes while stirring. This produced a yellow slurry which was stirred for two hours at 0° C. The ice bath was removed and the mixture allowed to warm to room temperature while stirring. The ether was removed from the slurry by evaporation under vacuum. Toluene (100 ml) was added to this solid and stirred for three hours at room temperature which resulted in a reddish slurry. The solids were filtered off using a fine fritted filter. The product was recovered from the toluene solution by evaporating the toluene under vacuum. The product was a dark red solid which contained 12.2 wt % Zr.

Polymerization Testing

A solution of the product was prepared by dissolving 0.3440 grams in 100 ml of toluene. Polymerizations were conducted as described in Example 1, except that 10.0 ml of 10% MAO in toluene was added as a cocatalyst and the polymerization was conducted at 80° C with 120 millimoles of hydrogen added. Five ml of the catalyst solution was used to start a polymerization and 11.1 grams of polymer was produced after one hour. The polymer had a MI of 0.082 dg/min and a HLMI of 4.51 dg/min. This corresponds to a MFR of 54.8.

EXAMPLE 14

This examples shows the effect of increased hydrogen on the catalyst activity. The polymerization described in Example 13 was repeated except that 180 millimoles of hydrogen were added to the reactor. The amount of polymer produced in 1 hour was 7.3 grams. The polymer had a MI of 0.071 dg/min and a HLMI of 2.90 dg/min. This corresponds to a MFR of 41.0.

EXAMPLE 15

This examples shows the effect of hydrogen and 1-butene on the catalyst activity. The polymerization described in Example 13 was repeated except that 120 millimoles of hydrogen and 20 ml of liquid 1-butene were added to the reactor. The amount of polymer produced in 1 hour was 8.5 grams. The polymer had a HLMI of 1.05 dg/min.

EXAMPLE 16

Carbazole (1.67 grams, from Aldrich Chemical Company) was recrystallized from ether and was placed in a 250-mL Schlenk flask which contained a stirring bar. The flask was sealed with a septum. Ether (100 mL) was added by double-ended needle. The solution was cooled to 0° C. in an ice bath. Methylmagnesium bromide (3.30 mL, 3.0 molar) in ether (from Aldrich Chemical Company) was added slowly by syringe while stirring. Gas evolved during this addition. The reaction mixture was stirred for one hour. The ice bath was removed and the mixture was allowed to warm to room temperature while stirring. The mixture was stirred an additional one hour at room temperature.

Zirconium tetrachloride (1.16 grams) from Aldrich Chemical Company (used without further purification) was placed in a clean, dry, oxygen-free 250-mL Schlenk flask which contained a stirring bar. The flask was sealed with a septum. 50 mL of ether was added by double-ended needle. This suspension was cooled to −78° C. in a dry ice/isopropanol bath. The carbazole/methylmagnesium bromide product was added to the ZrCl$_4$ suspension over ten minutes using a double-ended needle. The reaction mixture was stirred for one hour. The bath was removed and the mixture was allowed to warm to room temperature while stirring. The mixture was stirred an additional hour at room temperature. The product was a yellow-orange slurry.

The ether was removed from the slurry by evaporation under vacuum. Toluene (100 mL) was added to this solid and stirred for two hours at room temperature. The solution was recovered by vacuum filtration using a fine (4 micron) fritted glass filter. The toluene was removed by evaporation under vacuum. The product was a green solid which contained 8.1 wt % Zr.

Polymerization Results

Polymerizations were conducted in a stirred 1.7 liter stainless steel autoclave at 80° C. Dry, oxygen-free toluene (840 mL) was charged to the clean, dry, oxygen-free reactor and 6.0 mL of 10% methylaluminoxane (MAO) in toluene (from Ethyl Corporation and used without further purification) was added to the toluene in the reactor. No hydrogen or comonomer were added to the reactor. Sufficient ethylene was added to bring the reactor pressure to 150 psig. A solution of catalyst was prepared by dissolving 0.1090 grams of product in 100 mL of toluene. A polymerization was started by injecting 1.0 mL of this solution.

At the end of one hour the ethylene flow was stopped and the reactor rapidly cooled to room temperature. The polymer was filtered from the toluene by vacuum filtration. It was dried overnight in a vacuum oven and weighed. The weight of the polymer was 26.8 grams. This corresponded to a catalyst productivity of 304 kg/g Zr. The polymer had a MI of 0.136 dg/min and HLMI of 1.30 dg/min. This corresponds to a MFR of 9.6. This indicates a narrow molecular weight distribution even though the molecular weight was high.

EXAMPLE 17

The catalyst described in Example 16 was tested under the same polymerization conditions as Example 16 except that 25 mL of the catalyst solution was diluted to 100 mL with toluene. This diluted solution (1.0 mL) was used under the same conditions as Example 16. A one hour polymerization resulted in 38.3 grams of polyethylene. This corresponded to a catalyst productivity of 1,737 kg/g Zr. The polymer had a MI of 0.142 dg/min and HLMI of 1.45 dg/min. This corresponds to a MFR of 10.2. The polymer density was 0.9599 g/mL.

EXAMPLE 18

The catalyst described in Example 16 was tested under the same polymerization conditions as in Example 17 except that 20 mL of 10-butene was added as a comonomer. The 41.0 grams of polyethylene produced corresponded to a catalyst productivity of 1,859 kg/g Zr. The polymer had a MI of 0.154 dg/min and HLMI of 1.71 dg/min. This corresponds to a MFR of 11.1. The polymer density was 0.9411 g/mL.

EXAMPLE 19

The catalyst described in Example 16 was tested under the same polymerization conditions as in Example 17 except that 30 mmoles of hydrogen was added to the reactor. The 7.8 grams of polyethylene produced corresponded to a catalyst productivity of 354 kg/g Zr. The polymer had a MI of 197 dg/min. The polymer density was greater than 0.9700 g/mL.

EXAMPLE 20

Catalyst Preparation

The catalyst was prepared using the methods described in Example 16 except that 5.0 mL of a 1.0 molar solution of $TiCl_4$ in toluene was used in place of $ZrCl_4$. The product was a black solid which contained 8.7 wt % Ti.

Polymerization Testing

A solution of the product was prepared by dissolving 0.1065 grams in 100 mL of toluene. Polymerizations were conducted as described in Example 16. A polymerization was started using 1.0 mL of the catalyst solution and 18.1 grams of polymer was produced after one hour. This corresponded to a catalyst productivity of 196 kg/g Ti. The polymer had a MI of 0.150 dg/min and a HLMI of 1.60 dg/min. This corresponds to a MFR of 10.7.

EXAMPLE 21

The catalyst described in Example 20 was tested under the same polymerization conditions as Example 16 except that 25 mL of the catalyst solution was diluted to 100 mL with toluene. 1.0 mL of this diluted solution was used under the same conditions as Example 17. A one hour polymerization resulted in 10.0 grams of polyethylene. This corresponded to a catalyst productivity of 432 kg/g Ti. The polymer had a MI of 0.200 dg/min and HLMI of 1.64 dg/min. This corresponds to a MFR of 8.2.

EXAMPLE 22

The following example demonstrates the preparation of bis(carbazolyl)zirconium dichloride by the method of reacting tetrakis(diethylamido)zirconium with carbazole followed by chlorination with silicon tetrachloride.

Catalyst Preparation

All steps were conducted under an argon atmosphere using conventional Schlenk-line techniques. All glassware was clean and free of moisture and oxygen. All solvents were freed of water, air, and other impurities.

Carbazole (1.874 grams from Aldrich Chemical Company) was added at room temperature to a solution of 2.0 grams of tetrakis(diethylamido)zirconium dissolved in 40 ml of toluene. This was added over a ten minute period and stirred for three hours at room temperature. The volatiles were removed under vacuum. The resulting residue was dissolved in 30 mls of toluene. Silicon tetrachloride (0.954 grams) in 5.0 ml of toluene was added at room temperature. The mixture was stirred for four hours at room temperature. At the end of this period a greenish-yellow solid had separated from the initially brown solution. By evaporating the volatiles, 1.43 grams of solid was recovered. This was used without further purification.

Polymerization Results

Polymerizations were conducted in a stirred 1.7 liter stainless steel autoclave at 80° C. Dry, oxygen-free toluene (840 ml) was charged to the clean, dry, oxygen-free reactor. Six ml of 10% methylaluminoxane (MAO) in toluene (from Albemarle Corporation and used without further purification) was added to the toluene in the reactor. No hydrogen or comonomer were added. Sufficient ethylene was added to bring the reactor pressure to 150 psig. A solution of catalyst was prepared by dissolving 0.2508 grams of product in 100 ml of toluene. To start a polymerization 2.0 ml of this solution was injected into the reactor. At the end of one hour the ethylene flow was stopped and the reactor rapidly cooled to room temperature. The polymer was filtered from the toluene by vacuum filtration. It was dried overnight in a vacuum oven and weighed. The weight of the polymer was 9.1 grams. This corresponded to a catalyst productivity of 9.88 kg/g Zr. The polymer had a MI of 0.060 dg/min and HLMI of 0.36 dg/min. This corresponds to a MFR of 6.0 and indicates a narrow molecular weight distribution, even though the molecular weight was very high.

EXAMPLE 23

The catalyst described in Example 22 was tested under the same polymerization conditions as Example 22 except that 4.0 ml of the catalyst solution was used. A one hour polymerization resulted in 9.3 grams of polyethylene. This corresponded to a catalyst productivity of 5.05 kg/g Zr. The polymer had a MI of 0.0031 dg/min and HLMI of 0.097 dg/min. This corresponds to a MFR of 31.4.

Comparative Example 1

Catalyst Preparation

The catalyst was prepared using the methods described in Example 1. Pyrrole (from Aldrich Chemical Company) was distilled under nitrogen. Pyrrole (1.40 ml, 1.36 grams) was placed in a 250 ml Schlenk flask which contained a stirring bar. The flask was sealed with a septum. Diethyl ether (50 ml) was added by double-ended needle to dissolve the pyrrole. The solution was cooled to 0° C. in an ice bath and 6.70 ml of 3.0 molar methylmagnesium bromide in ether was added slowly by syringe while stirring. Gas evolved during this addition. The reaction mixture was stirred for 1 hour. The ice bath was removed and the mixture was allowed to warm to room temperature while stirring. The mixture was stirred an additional 1 hour at room temperature.

Zirconium tetrachloride (2.33 g) was placed in a clean, dry oxygen-free 250 ml Schlenk flask which contained a stirring bar. The flask was sealed with a septum and 100 ml of ether was added by double-ended needle. This suspension was cooled to 0° C. in an ice bath. The pyrrole/methylmagnesium bromide product was added to the $ZrCl_4$ suspension over 10 minutes using a double-ended needle. The reaction mixture was stirred for 1 hour. The ice bath was removed and the mixture was allowed to warm to room temperature while stirring. The mixture was stirred an additional hour at room temperature. The product was a yellow slurry.

The ether was removed from the slurry by evaporation under vacuum. This produced a brown solid. 100 ml of toluene was added to this solid and stirred for 2 hours at room temperature. The solution was recovered by vacuum filtration using a fine (4 micron) fritted glass filter. The toluene was removed by evaporation under vacuum. The amount of solid recovered was 0.453 g and it contained 15.1% Zr. Elemental analysis did not show the presence of Cl.

Polymerization Testing

A solution of the product was prepared by dissolving 0.3201 grams in 100 ml of toluene. Polymerizations were conducted as described in Example 1, except the 6.0 ml of 10% MAO in toluene was added as a cocatalyst and the polymerization was conducted at 110° C. No hydrogen or comonomer were added to the reactor. Five ml of the catalyst solution was used to start a polymerization and 24.3 grams of polymer was produced after one hour. The polymer had a MI of 1.20 dg/min and a HLMI of 27.86 dg/min. This corresponds to a MFR of 23.2.

Comparative Example 2

This example shows the low catalyst yield and low polymerization activities which result from using pyrrole derivatives which do not have aromatic rings fused to the pyrrole ring.

Catalyst Preparation

Dry, oxygen-free 2,5-dimethylpyrrole (1.90 grams, 99+%, from Aldrich Chemical Company) was placed in a clean dry, oxygen-free 4 ounce bottle with a stir bar and sealed with a rubber septum. Ether (50 ml) was added by syringe. The solution was cooled to 0° C. in an ice bath. Methylmagnesium bromide (6.7 ml of 3.0 molar) in ether (from Aldrich Chemical Company) was placed in a separate 4 ounce bottle and dissolved in 50 ml of ether. This methylmagnesium bromide/ether solution was slowly added to the 2,5-dimethylpyrrole solution using a double-edged needle while stirring. Gas evolved during this addition. The reaction mixture was stirred for 1 hour. The ice bath was removed and the mixture was allowed to warm to room temperature while stirring. The mixture was stirred an additional 1 hour at room temperature.

Zirconium tetrachloride (2.32 grams, from Aldrich Chemical Company and used without further purification) was placed in a clean, dry, oxygen-free 250 ml Schlenk flask which contained a stirring bar. The flask was sealed with a septum and 70 ml of dry, oxygen-free ether was added by syringe. This solution was cooled to 0° C. in an ice bath. The 2,5-dimethylpyrrole/methylmagnesium bromide product was added to the $ZrCl_4$ slurry over 10 minutes using a double-ended needle. The reaction mixture was stirred for about 2 hours. The bath was removed and the mixture was allowed to warm to room temperature while stirring. The mixture was stirred an additional hour at room temperature. The ether was evaporated and a tan solid product was recovered.

Toluene (100 ml) was added to this solid and stirred for 3 hours at room temperature. The solution was recovered by vacuum filtration using a fine (4 micron) fritted glass filter. The dissolved product was precipitated from solution by the addition of 700 ml of hexane. The solids were recovered by vacuum filtration using a fine fritted glass filter. Approximately 0.06 gram of light yellow solid was produced.

Polymerization Results

Polymerizations were conducted using the procedure described in Example 1. In this example 10.0 ml of 10% methylaluminoxane (MAO) in toluene (from Ethyl Corporation and used without further purification) was added to the toluene in the reactor. Hydrogen (180 mmoles) and no comonomer were added to the reactor. A solution of catalyst was prepared by dissolving 0.050 grams of product in 100 ml of toluene. Three ml of this solution was injected into the reactor to start a polymerization and 2.0 grams of polymer was produced.

Comparative Example 3

Catalyst Preparation

Distilled pyrrole (1.38 ml, from Aldrich Company) was placed in a clean, dry, oxygen-free 250 ml Schlenk flask with a stir bar and sealed with a rubber septum. Ether (40 ml) was added by syringe. The solution was cooled to 0° C. in an ice bath and 6.7 ml of 3.0 molar methylmagnesium bromide in ether (from Aldrich Chemical Company) was placed in a 4 ounce bottle and dissolved in 40 ml of ether. This methylmagnesium bromide/ether solution was slowly added to the pyrrole solution using a double-ended needle while stirring. Gas evolved during this addition. The reaction mixture was stirred for 1 hour. The ice bath was removed and the mixture was allowed to warm to room temperature while stirring. The mixture was stirred an additional 1 hour at room temperature.

Titanium tetrachloride (1.10 ml, from Aldrich Chemical Company) was dissolved in 30 ml of toluene in a clean, dry, oxygen-free 4 ounce bottle which contained a stirring bar. The bottle was sealed with a septum. The $TiCl_4$ solution was added to the pyrrole/methylmagnesium bromide product at 0° C. over 20 minutes using a double-ended needle. The reaction mixture was stirred for about 2 hours. The ice bath was removed and the mixture was allowed to warm to room temperature while stirring. The mixture was stirred an additional hour at room temperature. The ether was evaporated and a dark brown solid was recovered.

Toluene (100 ml) was added to this solid and stirred for 2 hours at room temperature. The solution was recovered by vacuum filtration using a fritted glass filter. The dissolved product was recovered by evaporating the toluene.

Polymerization Results

Polymerizations were conducted using the procedure described in Example 1 except that 10.0 ml of 10% methylaluminoxane (MAO) in toluene was added to the reactor along with 180 mmoles of hydrogen, but no comonomer. A solution of catalyst was prepared by dissolving 0.0960 grams of product in 100 ml of toluene. Three ml of this solution was injected into the reactor to start a polymerization and 3.4 grams of polymer was produced over one hour.

We claim:

1. A catalyst comprising a compound having the general formula $$[L]_m - M - [Y]_n$$
with $[Cp]_q$ above M and $[B]_p$ below M where L is a ligand, or mixture of ligands, each having 4 to 30 carbon atoms and containing at least two fused rings, one of which is a pyrrolyl ring, Cp is a ligand containing a cyclopentadienyl group, where two L ligands or an L and a Cp ligand can be bonded to each other via a bridging group, B is a Lewis base, Y is selected from the group consisting of halogen, alkoxy from $C_1$ to $C_{20}$, siloxy from $C_1$ to $C_{20}$, $N(R_1)_2$, and mixtures thereof, M is selected from the group consisting of titanium, zirconium, and mixtures thereof, $R_1$ is alkyl from $C_1$ to $C_{20}$, m is 2 to 4, n is 0 or 1, p is 0 or 2, q is 0 or 1, m+n+q=4, and m+q=3 or 4.

2. A catalyst according to claim 1 wherein M is titanium.
3. A catalyst according to claim 1 wherein M is zirconium.
4. A catalyst according to claim 1 wherein Y is halogen.
5. A catalyst according to claim 4 wherein Y is chlorine.
6. A catalyst according to claim 1 wherein L is indolyl or substituted indolyl and has the formula

[indolyl structure]—$(R)_s$ where each R is independently selected from hydrogen, alkyl from $C_1$ to $C_{10}$, and aryl from $C_6$ to $C_{10}$ and s is 1 to 4.

7. A catalyst according to claim 1 wherein L is carbazolyl or substituted carbazolyl and has the formula

[carbazolyl structure]—$(R)_s$ where each R is independently selected from hydrogen, alkyl from $C_1$ to $C_{10}$, and aryl from $C_6$ to $C_{10}$ and s is 1 to 4.

8. A catalyst according to claim 1 wherein m is 3.
9. A catalyst according to claim 1 wherein m is 4.
10. A catalyst according to claim 1 in combination with an organometallic cocatalyst.
11. A catalyst according to claim 10 wherein said organometallic cocatalyst is an aluminoxane.
12. A catalyst according to claim 10 in combination with one or more monomers polymerizable therewith.
13. A catalyst according to claim 12 wherein said monomer is ethylene.
14. A method of polymerizing an unsaturated olefinic monomer comprising contacting said monomer with the catalyst according to claim 10.
15. A catalyst comprising a compound having the general formula $$[L]_m - M - [X]_{4-m}$$

where L is a ligand containing an indolyl or carbazolyl group, M is selected from the group consisting of titanium, zirconium, and mixtures thereof, X is halogen, and m is 2, 3, or 4.

16. A catalyst according to claim 15 wherein M is titanium.
17. A catalyst according to claim 15 wherein M is zirconium.
18. A catalyst according to claim 15 wherein X is chlorine.
19. A catalyst comprising a compound having the general formula $$[L]_4 - M$$

where L is carbazolyl or indolyl with a $C_1$ to $C_4$ alkyl in the 2 position, the 7 position, or both the 2 and 7 positions, and M is titanium or zirconium.

20. A catalyst comprising a compound having the general formula $$[L]_m - M - [X]_n$$

where L is a ligand, or mixture of ligands, each having 4 to 30 carbon atoms and containing at least two fused rings, one of which is a pyrrolyl ring, where two L ligands can be bonded to each other via a bridging group, X is halogen, M is selected from the group consisting of titanium, zirconium, and mixtures thereof, m is 2 to 4, n is 0 to 2, and m+n is 4.

21. A catalyst according to claim 20 wherein m is 3 and n is 1.

22. A catalyst according to claim 20 wherein m is 4 and n is 0.

* * * * *